United States Patent
Tanaka

(10) Patent No.: US 10,976,254 B2
(45) Date of Patent: Apr. 13, 2021

(54) FIRE DETECTION SYSTEM, RECEIVER, AND FIRE DETECTION METHOD

(71) Applicant: NEC Corporation, Tokyo (JP)

(72) Inventor: Akihiro Tanaka, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 16/623,486

(22) PCT Filed: Jun. 27, 2017

(86) PCT No.: PCT/JP2017/023486
§ 371 (c)(1),
(2) Date: Dec. 17, 2019

(87) PCT Pub. No.: WO2019/003288
PCT Pub. Date: Jan. 3, 2019

(65) Prior Publication Data
US 2020/0191716 A1 Jun. 18, 2020

(51) Int. Cl.
*G01N 21/61* (2006.01)
*G01N 33/00* (2006.01)

(52) U.S. Cl.
CPC ......... *G01N 21/61* (2013.01); *G01N 33/0022* (2013.01); *G01N 33/0062* (2013.01)

(58) Field of Classification Search
CPC .... G01N 21/53; G01N 21/61; G01N 33/0022; G01N 33/0062; G01N 21/3504; G08B 17/00
USPC ................................. 356/432–444
See application file for complete search history.

(56) References Cited

U.S. PATENT DOCUMENTS

| 2009/0229250 A1* | 9/2009 | Yamakage | G01N 21/532 60/276 |
| 2011/0188039 A1* | 8/2011 | Aoyama | G01N 21/53 356/338 |
| 2017/0169683 A1 | 6/2017 | Ryder | |

FOREIGN PATENT DOCUMENTS

| JP | 06109631 A | 4/1994 |
| JP | 2000504132 A | 4/2000 |
| JP | 2005083876 A | 3/2005 |

(Continued)

OTHER PUBLICATIONS

International Search Report dated Sep. 19, 2017 from the International Bureau in application No. PCT/JP2017/023486.

(Continued)

*Primary Examiner* — Tri T Ton

(57) ABSTRACT

A fire detection system includes: a transmitter to output a first optical signal including a wavelength absorbed by a first gas generated in an early stage of a fire and a second optical signal including a wavelength absorbed by a second gas having an amount of generation being increased as the fire progresses; and a receiver including a detector to receive the first optical signal and the second optical signal propagating through a measuring target space, a first gas concentration calculator to calculate a concentration of the first gas, a second gas concentration calculator to calculate a concentration of the second gas, a smoke concentration calculator to calculate a smoke concentration, and a determination unit to determine progress of the fire, based on the concentration of the first gas, the concentration of the second gas, the smoke concentration, and an environmental temperature.

20 Claims, 11 Drawing Sheets

(56) References Cited

FOREIGN PATENT DOCUMENTS

JP 2008225857 A 9/2008
JP 2016537647 A 12/2016

OTHER PUBLICATIONS

"16.3 Line Widths", Atkins' Physical Chemistry, Spectroscopy 1: Rotational and Vibrational Spectra, (vol. two), Tokyo Kagaku Doujin Co., Ltd. Apr. 10, 2001, pp. 495-501.
"3.3 Visible-ultraviolet Spectrum of Gas Phase", Visible-ultraviolet Spectrometry, Introduction Series 5 to Spectrometry, Kodansha Scientific, Co., Ltd., Apr. 10, 2009, pp. 54-75.
Heskestad, G., et al., "Fire Detection Using Cross-Correlations of Sensor Signals", Fire Safety Journal, vol. 18, 1992, No. 4, pp. 355-374.
Chen, S.-J., et al., "Fire detection using smoke and gas sensors", Fire Safety Journal, vol. 42, No. 8, 2007, pp. 507-515.
Ichoku, C., et al., "Laboratory investigation of fire radiative energy and smoke aerosol emissions", Journal of Geophysical Research, vol. 113, No. D14, 2008, pp. 1-11.

\* cited by examiner

FIRE DETECTION SYSTEM, RECEIVER, AND FIRE DETECTION METHOD

This application is a National Stage Entry of PCT/JP2017/023486 filed on Jun. 27, 2017, the contents of all of which are incorporated herein by reference, in their entirety.

TECHNICAL FIELD

The present invention relates to a fire detection system, a receiver, and a fire detection method, and more particularly, to a fire detection system, a receiver, and a fire detection method that make a determination about a fire situation by propagating an optical signal.

BACKGROUND ART

Inside a tunnel of a road, underground station premises, and the like, there is used a fire detection system for quickly and accurately detecting an outbreak of a fire and issuing an alarm without providing many sensors, and making a determination about a fire situation by propagating an optical signal in order to safely evacuate a user.

For example, PTL 1 discloses a disaster preventing system that includes a laser irradiation means for making irradiation with a laser beam near an absorption wavelength by carbon monoxide inside underground station premises and a laser reception means for receiving the irradiated laser beam inside the underground station premises, and calculates a concentration of carbon monoxide inside the underground station premises by a laser absorption method. Further, the disaster preventing system disclosed in PTL 1 calculates a transmittance of fumes by taking a ratio of irradiated incident light to received transmitted light, and issues a fire alarm from a central control unit when measurement values of the calculated concentration of carbon monoxide and the calculated transmittance of fumes exceed predetermined values.

Further, PTL 2 discloses a fire alarm device that irradiates a smoke detection space with light with wavelengths of two types, and determines a smoke type, based on a ratio of light intensities of scattered light of the light with the respective wavelengths when the smoke enters. Further, the fire alarm device disclosed in PTL 2 irradiates a smoke detection space with light with a plurality of wavelengths, detects, via an optical filter, light with wavelengths of two specific types from scattered light when smoke enters, and determines the smoke type, based on a ratio of light intensities of the light with the respective wavelengths. Furthermore, the fire alarm device determines presence or absence of a fire by further comparing a threshold value set according to the determined smoke type with the light intensities.

CITATION LIST

Patent Literature

[PTL 1] Japanese Unexamined Patent Application Publication No. 2005-83876
[PTL 2] Japanese Unexamined Patent Application Publication No. H06-109631

SUMMARY OF INVENTION

Technical Problem

Urgency can be determined when a degree of progress of a fire can be perceived, and a wider range of fire scenarios can be handled. In the fire detection method in PTL 1, since a fire alarm is issued when an amount of smoke and an amount of carbon monoxide exceed threshold values, it is difficult for an administrator to perceive whether it is before or after a fire breaks out.

Further, mixing ethanol (bioethanol) into fuel of automobiles at a ratio equal to or greater than a certain ratio is stipulated by law in foreign countries. As the ratio of mixed ethanol increases, smoke and carbon monoxide generated during combustion decrease. In the fire detection method in PTL 1, since a fire alarm is issued when an amount of smoke and an amount of carbon monoxide exceed threshold values, accurate fire detection may not be performed in a fire of an automobile using fuel having a great ratio of mixed ethanol.

Further, in the configuration disclosed in PTL 2, since a smoke concentration is a basis for determination, it is difficult to clearly perceive a degree of progress of a fire as to whether before or after the fire breaks out. Furthermore, since a smoke concentration is a basis for determination, the fire detection device disclosed in PTL 2 does not react to a fire having a small generation amount of smoke.

The present invention has been made in view of the problem above, and one object thereof is to provide a fire detection system, a receiver, and a fire detection method, being capable of determining a degree of progress of a fire and handling a wider range of fire scenarios in the fire detection system, the receiver, and the fire detection method that monitor a situation of an outbreak of a fire by propagating an optical signal.

Solution to Problem

A fire detection system according to one aspect of the present invention includes: a transmitter including a light source that emits a first optical signal including a wavelength absorbed by a first gas generated in an early stage of a fire and a second optical signal including a wavelength absorbed by a second gas generated after the fire progresses; a detection unit that receives the first and second optical signals propagating through a measuring target space; and a receiver including a first gas concentration calculation unit that calculates a concentration of the first gas from an intensity of the first optical signal propagating through the measuring target space, a second gas concentration calculation unit that calculates a concentration of the second gas from an intensity of the second optical signal propagating through the measuring target space, a smoke concentration calculation unit that calculates a smoke concentration from the intensities of the first and second optical signals propagating through the measuring target space, and a determination unit that determines a fire situation, based on the concentration of the first gas, the concentration of the second gas, and the smoke concentration.

A receiver according to another aspect of the present invention includes a detection unit that receives a first optical signal including a wavelength absorbed by a first gas generated in an early stage of a fire and a second optical signal including a wavelength absorbed by a second gas generated after the fire progresses, a first gas concentration calculation unit that calculates a concentration of the first gas from an intensity of the received first optical signal, a second gas concentration calculation unit that calculates a concentration of the second gas from an intensity of the received second optical signal, a smoke concentration calculation unit that calculates a smoke concentration from the intensities of the received first and second optical signals, and a determination unit that determines a fire situation, based on the concentration of the first gas, the concentration of the second gas, and the smoke concentration.

A fire detection method according to still another aspect of the present invention includes: receiving a first optical signal propagating through a measuring target space and a second optical signal that propagates through the measuring target space and has a wavelength different from that of the first optical signal; calculating a concentration of a first gas from an intensity of the received first optical signal; calculating a concentration of a second gas from an intensity of the received second optical signal; calculating a smoke concentration from the intensities of the received first and second optical signals; and determining a fire situation, based on the concentration of the first gas, the concentration of the second gas, and the smoke concentration.

Advantageous Effects of Invention

According to the above-described aspects of the present invention, a degree of progress of a fire can be perceived, and a wider range of fire scenarios can be handled, in the fire detection system, the receiver, and the fire detection method that monitor a situation of an outbreak of a fire by propagating an optical signal.

EXAMPLE EMBODIMENT

Figure 1:
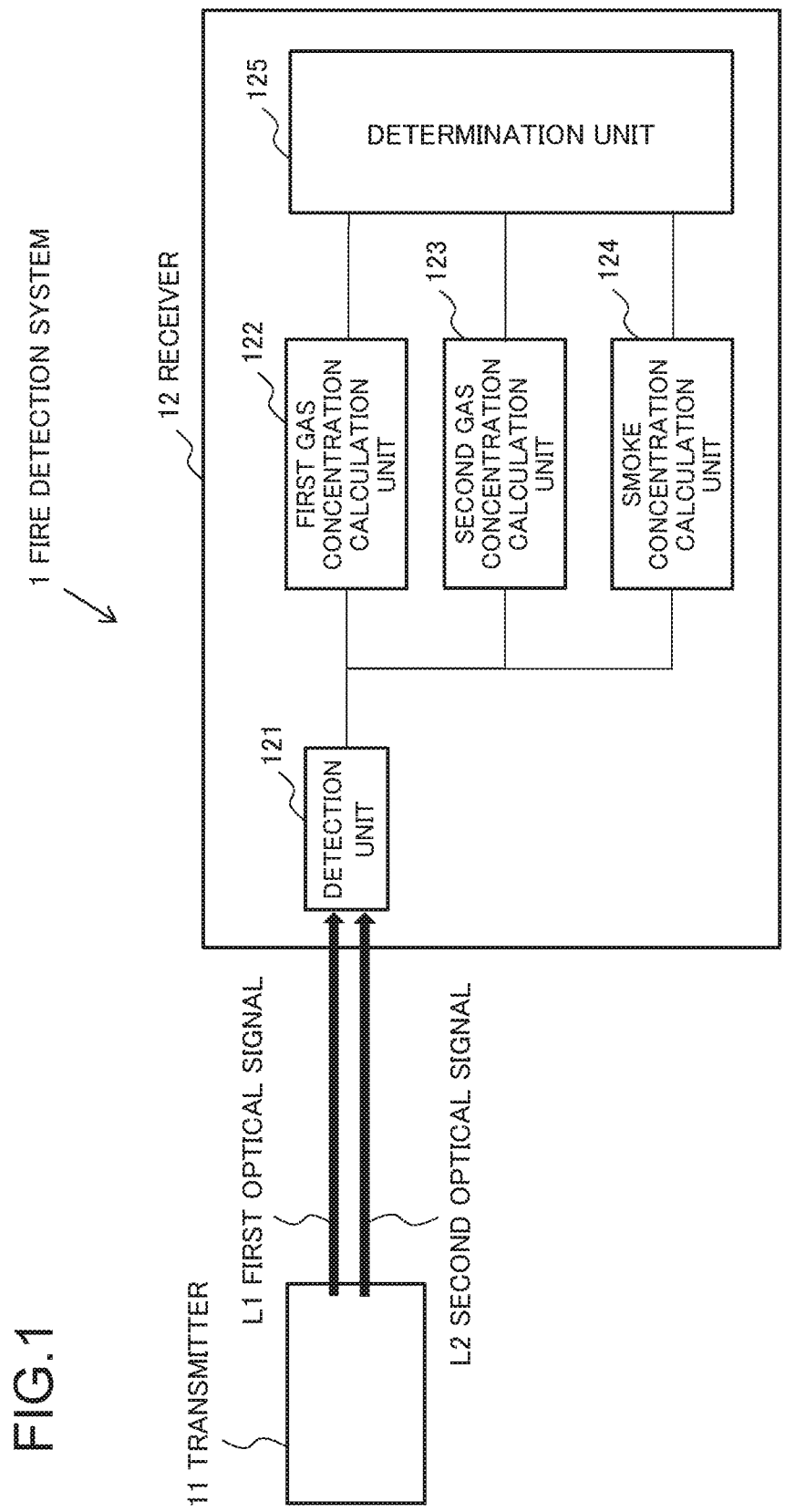
FIG. 1 is a block diagram illustrating a configuration of a first example embodiment.

Next, example embodiments according to the present invention will be described in detail with reference to drawings.
Configuration of First Example Embodiment FIG. 1 is a block diagram illustrating a configuration of a first example embodiment. As illustrated in FIG. 1, a fire detection system 1 is constituted of a transmitter 11 and a receiver 12. The transmitter 11 emits, into a measuring target space, two kinds of optical signals (hereinafter referred to as a first optical signal L1 and a second optical signal L2) respectively including wavelengths absorbed by two kinds of gases (hereinafter referred to as a first gas and a second gas) generated in a fire. The first gas is a gas generated in an early stage of a fire and is, for example, carbon monoxide. The second gas is a gas having a generation amount being increased as the fire progresses and is, for example, carbon dioxide. Further, for example, similarly to carbon dioxide, the second gas may be a gas generated in a great amount even in a fire having a small generation amount of the first gas. The first gas is not limited to carbon monoxide, and only needs to be a gas generated in an early stage of a fire. The second gas is not limited to carbon dioxide, and only needs to be a gas having a generation amount being increased as the fire progresses after the generation of the first gas. Further, for example, the transmitter 11 may be configured to include a laser light source that outputs the optical signal L1 including a wavelength $\lambda_1$ absorbed by the first gas, and a laser light source that outputs the optical signal L2 including a wavelength $\lambda_2$ absorbed by the second gas. Alternatively, the transmitter 11 may be configured to include one laser light source capable of controlling a wavelength by input signals and capable of alternately outputting the first optical signal L1 and the second optical signal L2 by alternately switching the input signals.

As illustrated in FIG. 1, the receiver 12 includes a detection unit 121, a first gas concentration calculation unit 122, a second gas concentration calculation unit 123, a smoke concentration calculation unit 124, and a determination unit 125 that determines a progress situation of a fire based on a concentration of a first gas, a concentration of a second gas, and a smoke concentration.

The detection unit 121 receives the first optical signal L1 and the second optical signal L2 that are emitted from the transmitter 11 and propagate through the measuring target space. The detection unit 121 may be configured to include, for example, a sensor having sensitivity to the wavelength $\lambda_1$ absorbed by the first gas and a sensor having sensitivity to the wavelength $\lambda_2$ absorbed by the second gas.

The first gas concentration calculation unit 122 calculates a concentration of the first gas from an intensity of the received first optical signal L1 output from the detection unit 121, and outputs the concentration to the determination unit 125. A spectrum of an optical signal propagating through a measuring target space has a transmittance decreasing abruptly at a wavelength absorbed by gas present in the measuring target space, and a decrease in transmittance becomes larger with a greater concentration of the gas. For example, an intensity of the first optical signal L1 output from the transmitter is preset in the first gas concentration calculation unit 122. When the intensity of the optical signal L1 propagating through the measuring target space is input from the detection unit 121, the first gas concentration calculation unit 122 acquires a transmittance in a predetermined wavelength range including the wavelength $\lambda_1$ absorbed by the first gas. The first gas concentration calculation unit 122 calculates a concentration of the first gas from the transmittance.

The second gas concentration calculation unit 123 calculates a concentration of the second gas from an intensity of the received second optical signal L2, similarly to the first gas concentration calculation unit 122. For example, the intensity of the second optical signal L2 output from the transmitter is preset in the second gas concentration calculation unit 123. When the intensity of the optical signal L2 propagating through the measuring target space is input from the detection unit 121, the second gas concentration calculation unit 123 acquires a transmittance in a predetermined wavelength range including the wavelength $\lambda_2$ absorbed by the second gas. The second gas concentration calculation unit 123 calculates a concentration of the second gas from the transmittance.

The smoke concentration calculation unit 124 calculates a smoke concentration Cs based on an equation (1) below.

$$Is = Io \times e^{-CsD} \tag{1}$$

Herein, Io is an intensity of an optical signal output from the transmitter 11, and Is is an intensity of the optical signal received by the receiver 12. Further, D is a distance between the transmitter 11 and the receiver 12. Note that a transmittance of the optical signal is Is/Io. Intensities $Io_1$ and $Io_2$ of the first and second optical signals L1 and L2 output from the transmitter are preset in the smoke concentration calculation unit 124. The smoke concentration calculation unit 124 calculates a transmittance in a measuring target space from at least one of intensities $Is_1$ and $Is_2$ of the first and second optical signals L1 and L2 propagating through the measuring target space from the detection unit 121. The smoke concentration calculation unit 124 may output a smoke concentration calculated by the equation (1) from either the intensity $Is_1$ of the first optical signal L1 or the intensity $Is_2$ of the second optical signal L2. Alternatively, the smoke concentration calculation unit 124 may calculate smoke concentrations $Cs_1$ and $Cs_2$ calculated by the equation (1) from both of the intensities $Is_1$ and $Is_2$ of the first and second optical signals L1 and L2, and output the smoke concentration Cs by averaging the smoke concentrations $Cs_1$ and $Cs_2$. Then, the smoke concentration calculation unit 124 calculates the smoke concentration in the measuring target space from the calculated transmittance in the measuring target space.

The determination unit 125 determines a fire situation based on a concentration of the first gas, a concentration of the second gas, and a smoke concentration. For example, the determination unit 125 determines whether a concentration of the first gas is greater than a preset threshold value. When the concentration of the first gas is greater than the threshold value, the determination unit 125 determines whether a smoke concentration is greater than a preset threshold value. When the smoke concentration is greater than the threshold value, the determination unit 125 determines that a fire breaks out. When it is determined that a fire breaks out, the determination unit 125 determines whether a concentration of the second gas is greater than a preset threshold value. When the concentration of the second gas is smaller than the threshold value, the determination unit 125 determines that it is a sign of a fire, and calls a monitor's attention. When the concentration of the second gas is greater than the threshold value, the determination unit 125 determines that a fire is in progress, and issues an alarm to the monitor. Further, when the concentration of the first gas is smaller than the threshold value, the determination unit 125 determines whether the concentration of the second gas is greater than the preset threshold value. When the concentration of the second gas is greater than the threshold value, the determination unit 125 determines that it is detection of a fire, and issues an alarm to the monitor.

Figure 11:
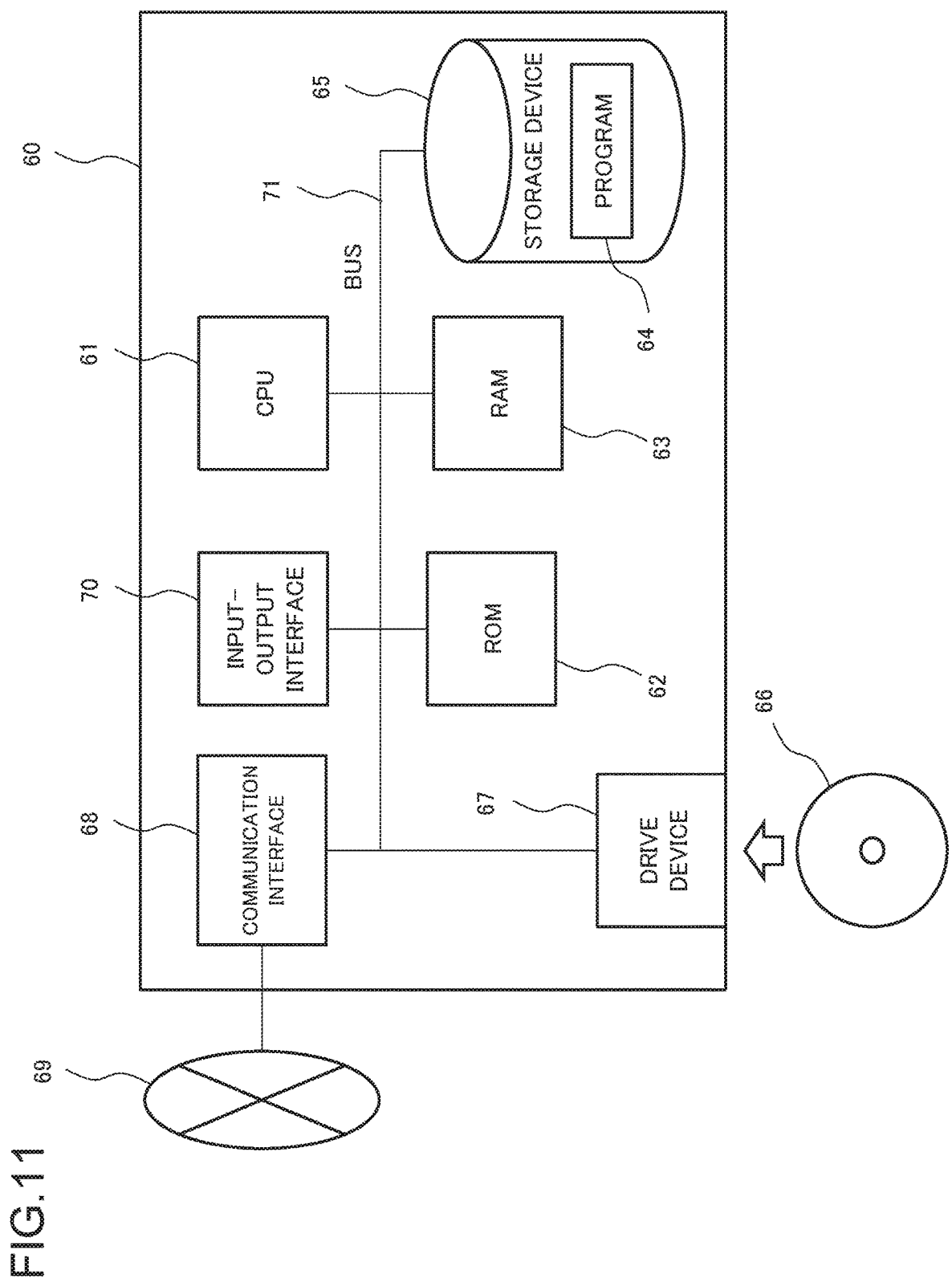
FIG. 11 is a block diagram illustrating a configuration of a computer that achieves a function of each unit in each of the example embodiments.

Note that each component in the first example embodiment illustrated in FIG. 1 and the like and each example embodiment to be described later represents a block of a functional unit. A part or all of each component in the first example embodiment and each example embodiment to be described later may be achieved by any combination of a computer 60 and a program as illustrated in FIG. 11, for example. The computer 60 includes the following configuration as one example.

A central processing unit (CPU) 61,
a read only memory (ROM) 62,
a random access memory (RAM) 63,
a program 64 loaded into the RAM 63,
a storage device 65 that stores the program 64,
a drive device 67 that reads from and writes to a recording medium 66,
a communication interface 68 coupled to a communication network 69,
an input-output interface 70 that inputs and outputs data, and
a bus 71 that couples components.

A function of each of the components in the first example embodiment and each example embodiment to be described later is achieved by the CPU 61 acquiring and executing the program 64 that achieves the functions thereof. The program 64 that achieves the function of each of the components is previously stored in the storage device 65, the ROM 62, or the RAM 63, for example, and is read by the CPU 61 as necessary.

Note that the program 64 may be supplied to the CPU 61 via the communication network 69, or may be previously stored in the recording medium 66 and read by the drive device 67 to be supplied to the CPU 61.

There are various modification examples for a method of achieving a function of each of the components in the first example embodiment and each example embodiment to be described later. For example, the function of each of the components may be achieved by any combination of a computer and a program, which differs by each of the components. Further, the function of each of the components may be achieved by any combination of one computer and a program.

Further, a part or all of each of the components in the first example embodiment and each example embodiment to be described later may be achieved by another general-purpose or dedicated circuitry, a processor, and the like, or a combination thereof. A part or all of each of the components may be formed by a single chip or formed by a plurality of chips coupled one another via a bus. Further, a part or all of each of the components may be achieved by a combination of the above-described circuitry and the like and a program.

When a part or all of each of the components in the first example embodiment and each example embodiment to be described later is achieved by a plurality of computers, circuits, or the like, the plurality of computers, circuits, or the like may be arranged in a concentrated manner or a distributed manner. For example, the computer, the circuit, or the like may be achieved as a form in which each is coupled via a communication network.

(Operation in First Example Embodiment)

Figure 2:
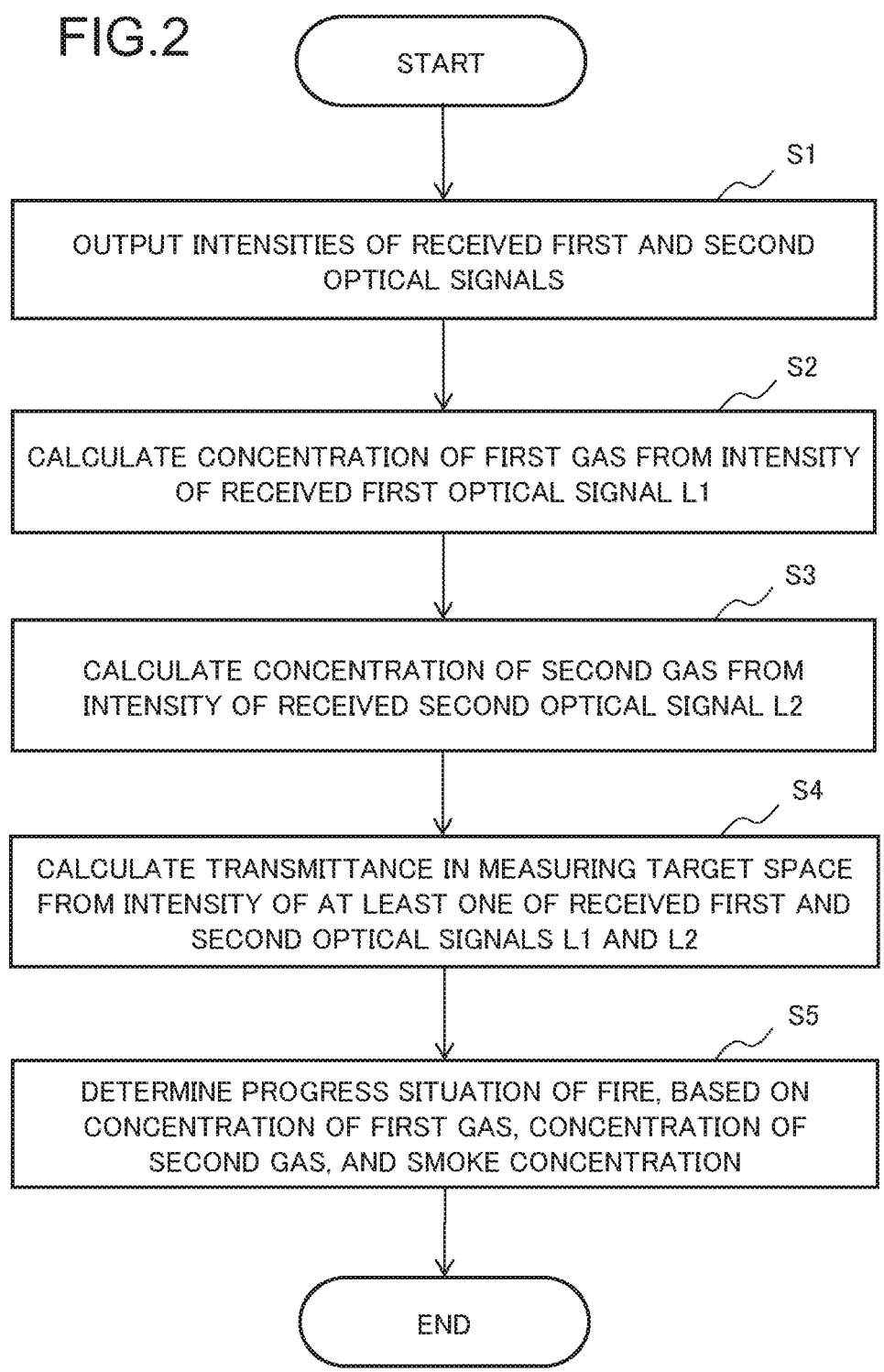
FIG. 2 is a flowchart illustrating an operation of FIG. 1.

FIG. 2 is a flowchart illustrating an operation of the receiver in FIG. 1. When the transmitter 11 emits the first optical signal L1 and the second optical signal L2 into a measuring target space between the transmitter 11 and the receiver 12, the detection unit 121 of the receiver 12 receives the first and second optical signals L1 and L2 propagating through the measuring target space between the transmitter 11 and the receiver 12. The detection unit 121 outputs intensities of the received first and second optical signals L1 and L2, that is, electric signals acquired by performing photoelectric conversion on the first and second optical signals L1 and L2, for example, to the first gas concentration calculation unit 122, the second gas concentration calculation unit 123, and the smoke concentration calculation unit 124 (Step S1).

The first gas concentration calculation unit 122 calculates a concentration of a first gas from the intensity of the received first optical signal L1, and outputs the concentration to the determination unit 125 (Step S2). Further, the second gas concentration calculation unit 123 calculates a concentration of a second gas from the intensity of the received second optical signal L2, and outputs the concentration to the determination unit 125 (Step S3).

Further, the smoke concentration calculation unit 124 calculates a smoke concentration in the measuring target space from the intensity of at least one of the received first and second optical signals L1 and L2 output from the detection unit 121, and outputs the smoke concentration to the determination unit 125 (Step S4).

The determination unit 125 determines a fire situation based on the concentration of the first gas output from the first gas concentration calculation unit 122, the concentration of the second gas output from the second gas concentration calculation unit 123, and the smoke concentration output from the smoke concentration calculation unit 124 (Step S5).

According to the first example embodiment as described above, in addition to an increase in a concentration of the first gas generated in an early stage of a fire and a smoke concentration, a concentration of the second gas having a generation amount being increased as the fire progresses is also added as a determination indicator, and a progress situation of the fire is determined. In this way, an urgent response can be achieved while the progress situation of the fire is also taken into consideration. Further, by also adding a concentration of the second gas different from the first gas as a determination indicator, a fire difficult to detect with only a concentration of the first gas and a smoke concentration, for example, can be detected when a generation amount of the second gas is large, and a wider range of fire scenarios can be handled.

(Configuration of Second Example Embodiment)

Next, a second example embodiment according to the present invention will be described in detail with reference to drawings.

Figure 3:
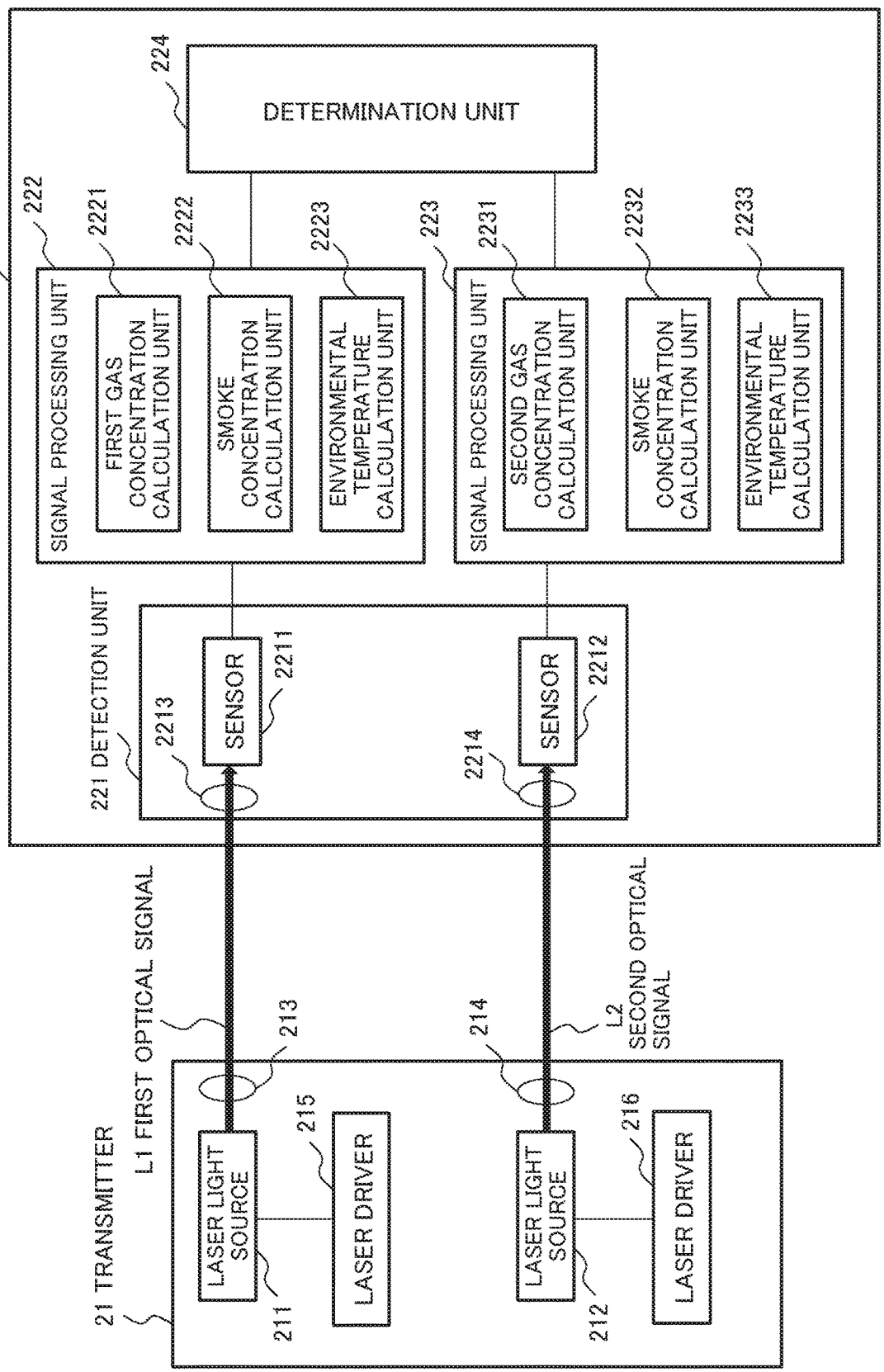
FIG. 3 is a block diagram illustrating a configuration of a second example embodiment according to the present invention.

FIG. 3 is a block diagram illustrating a configuration of the second example embodiment. An optical signal propagates between a transmitter 21 and a receiver 22, and a gas concentration, a smoke concentration, and a temperature of a measuring target in a space between the transmitter 21 and the receiver 22 are measured.

The transmitter 21 is formed of: a laser light source 211 that emits, into a measuring target space, a first optical signal L1 having a predetermined wavelength range including an absorption spectrum of a first gas; a laser light source 212 that emits, into the measuring target space, a second optical signal L2 having a predetermined wavelength range including an absorption spectrum of a second gas; condensers 213 and 214 that condense the optical signals L1 and L2 emitted from the laser light sources 211 and 212, respectively; and laser drivers 215 and 216 that drive the laser light sources 211 and 212, respectively. The condensers 213 and 214 convert light output from the laser light sources 211 and 212, respectively, into quasi-parallel light beams. The laser drivers 215 and 216 control drive currents and temperatures of the laser light sources 211 and 212, respectively.

The receiver 22 is formed of: a detection unit 221 configured to include two sensors of a sensor 2211 having sensitivity to the absorption spectrum of the first gas and a sensor 2212 having sensitivity to the absorption spectrum of the second gas; two signal processing units 222 and 223; and a determination unit 224. Further, the detection unit 221 includes condensers 2213 and 2214 that focus the received optical signals L1 and L2 on the sensors 2211 and 2212, respectively. The sensors 2211 and 2212 perform photoelectric conversion on the received optical signals L1 and L2, and output the optical signals L1 and L2 to the signal processing units 222 and 223, respectively.

The signal processing unit 222 includes: a first gas concentration calculation unit 2221 that calculates a concentration of the first gas from an intensity of the received first optical signal L1; a smoke concentration calculation unit 2222 that calculates a smoke concentration from the intensity of the received first optical signal L1; and an environmental temperature calculation unit 2223 that calculates an environmental temperature from the intensity of the received first optical signal L1. Further, the signal processing unit 223 includes: a second gas concentration calculation unit 2231 that calculates a concentration of the second gas from an intensity of the received second optical signal L2; a smoke concentration calculation unit 2232 that calculates a smoke concentration from the intensity of the received second optical signal L2; and an environmental temperature calculation unit 2233 that calculates an environmental temperature from the intensity of the received second optical signal L2.

Figure 4:
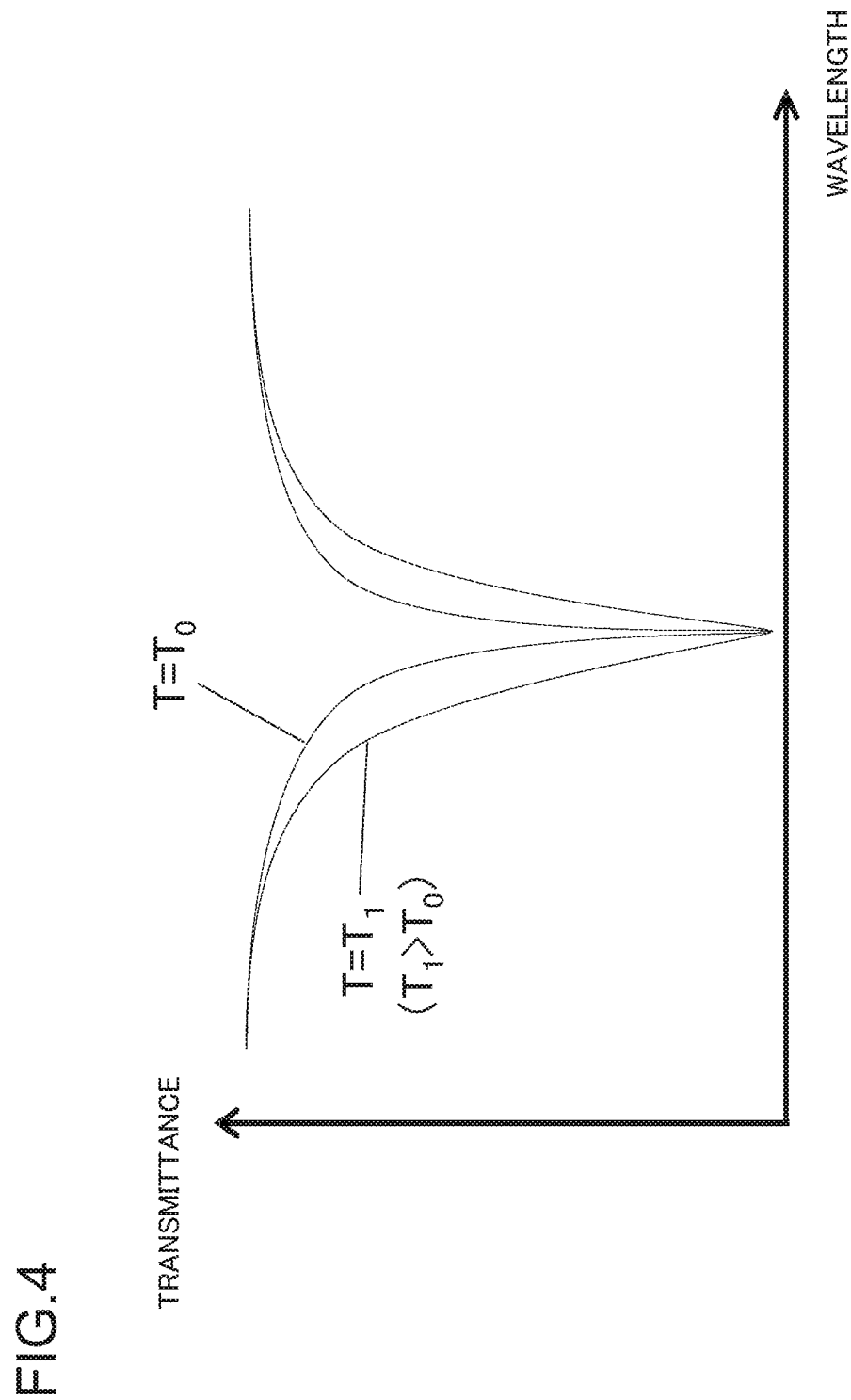
FIG. 4 is a schematic diagram illustrating a shape change of an absorption spectrum due to an environmental temperature.

The environmental temperature calculation units 2223 and 2233 calculate an environmental temperature from the intensities of the received first and second optical signals L1 and L2. FIG. 4 is a schematic diagram illustrating a shape change of an absorption spectrum due to an environmental temperature. A shape of an absorption spectrum of a gas molecule changes due to an environmental temperature, atmospheric pressure, and an interaction with another gas molecule. In particular, a change in spectral width due to a change in environmental temperature is conspicuous. A higher environmental temperature T increases a velocity distribution of gaseous molecules, and a width of an absorption spectrum is increased due to Doppler broadening when $T=T_1$ (note that $T_1>T_0$) more than when $T=T_0$ as illustrated in FIG. 4. The environmental temperature calculation units 2223 and 2233 calculate spectral widths of the received first and second optical signals L1 and L2 from the intensities (spectra) of the received first and second optical signals L1 and L2, and perform a measurement of the environmental temperature T in the measuring target space. Note that a measurement of the environmental temperature T in the measuring target space may be performed by a method other than a method of measuring an environmental temperature from a change in absorption spectrum width, and a different method such as a laser induced fluorometry, for example, may be used.

(Operation in Second Example Embodiment)

Figure 5:
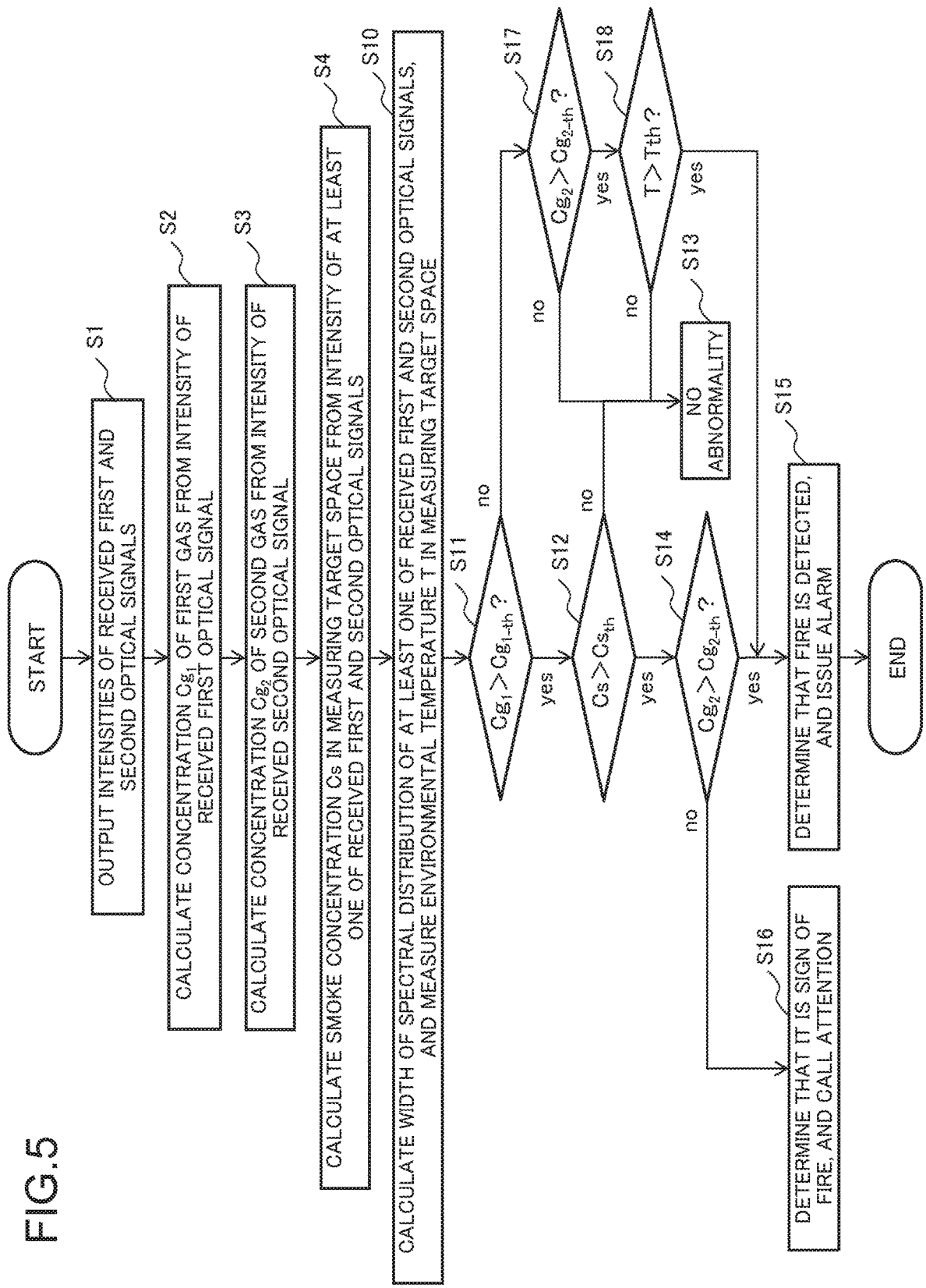
FIG. 5 is a flowchart illustrating an operation of FIG. 3.

FIG. 5 is a flowchart illustrating an operation of FIG. 3. When the laser light sources 211 and 212 of the transmitter 21 respectively emit the first optical signal L1 and the second optical signal L2 into the measuring target space, the sensor 2211 of the detection unit 221 of the receiver 22 receives the first optical signal L1 propagating through the measuring target space, and the sensor 2212 of the detection unit 221 receives the second optical signal L2 propagating through the measuring target space. The sensor 2211 of the detection unit 221 outputs an intensity of the received first optical signal L1 to the signal processing unit 222, and the sensor 2212 of the detection unit 221 outputs an intensity of the received second optical signal L2 to the signal processing unit 223 (Step S1).

The first gas concentration calculation unit 2221 of the signal processing unit 222 calculates a concentration $Cg_1$ of a first gas from the intensity of the received first optical signal L1, and outputs the concentration $Cg_1$ to the determination unit 224 (Step S2). Further, the second gas concentration calculation unit 2231 calculates a concentration $Cg_2$ of a second gas from the intensity of the received second optical signal L2, and outputs the concentration $Cg_2$ to the determination unit 224 (Step S3). The concentration $Cg_1$ of the first gas and the concentration $Cg_2$ of the second gas may be average values acquired by respectively measuring the first and second gas concentrations for a predetermined period of time.

Further, the smoke concentration calculation unit 2222 of the signal processing unit 222 calculates a smoke concentration in the measuring target space from the intensity of the received first optical signal L1, and outputs the smoke concentration to the determination unit 224. Further, the smoke concentration calculation unit 2232 of the signal processing unit 223 calculates a smoke concentration in the measuring target space from the intensity of the received second optical signal L2, and outputs the smoke concentration to the determination unit 224 (Step S4).

Then, in the present example embodiment, the environmental temperature calculation unit 2223 calculates a spectral width of the received first optical signal L1 from the intensity (spectrum) of the received first optical signal L1, and performs a measurement of an environmental temperature T in the measuring target space. Further, the environmental temperature calculation unit 2233 calculates a spectral width of the received second optical signal L2 from the intensity (spectrum) of the received second optical signal L2, and performs a measurement of the environmental temperature T in the measuring target space (Step S10). Note that a measurement of the environmental temperature T in the measuring target space may be performed by a method other than a method of measuring an environmental temperature from a change in absorption spectrum width, and a different method such as a laser induced fluorometry, for example, may be used.

Next, the determination unit 224 performs a comparison between the concentration $Cg_1$ of the first gas and a preset threshold value $Cg_{1\_th}$ to (Step S11). When the concentration $Cg_1$ of the first gas exceeds the threshold value $Cg_{1\_th}$, the determination unit 224 calculates the smoke concentration Cs from at least one of a smoke concentration $Cs_1$ from the smoke concentration calculation unit 2222 of the signal processing unit 222 and a smoke concentration $Cs_2$ from the smoke concentration calculation unit 2232 of the signal processing unit 223, and performs a comparison between the smoke concentration Cs and a preset threshold value $Cs_{th}$ (Step S12). When the smoke concentration Cs is equal to or less than the threshold value $Cs_{th}$, the determination unit 224 determines that there is no abnormality (Step S13). For example, when the first gas is carbon monoxide, this is related to a case in which a concentration of the first gas in a tunnel rises due to exhaust gas of an automobile, and the like.

When the smoke concentration Cs exceeds the threshold value $Cs_{th}$ in Step S12, the determination unit 224 further performs a comparison between the concentration $Cg_2$ of the second gas and a preset threshold value $Cg_{2\_th}$ (Step S14). When the concentration $Cg_2$ of the second gas exceeds the threshold value $Cg_{2\_th}$, the determination unit 224 determines that a fire is detected, and issues an alarm to a monitor (Step S15).

When the concentration $Cg_2$ of the second gas is equal to or less than the threshold value $Cg_{2\_th}$ in Step S14, the determination unit 224 determines that a sign of a fire is detected, and calls the monitor's attention (Step S16). For example, when the first gas is carbon monoxide, this is related to a case in which carbon monoxide is mainly generated before a fire breaks out, and the like.

Next, when the concentration $Cg_1$ of the first gas is equal to or less than the threshold value $Cg_{1\_th}$ in Step S11, the determination unit 224 performs a comparison between the concentration $Cg_2$ of the second gas and the preset threshold value $Cg_{2\_th}$ (Step S17). When the concentration $Cg_2$ of the second gas exceeds the threshold value $Cg_{2\_th}$, the determination unit 224 performs a comparison between the measured environmental temperature T and a preset threshold value $T_{th}$ (Step S18).

When the environmental temperature T exceeds the threshold value $T_{th}$, the processing proceeds to Step S15, and the determination unit 224 determines that a fire is detected, and issues an alarm. When the environmental temperature T is equal to or less than the threshold value $T_{th}$, the processing proceeds to Step S13, and it is determined that there is no abnormality. For example, when the second gas is carbon dioxide, this is related to a case in which exhaust gas of an automobile or a vehicle loaded with dry ice as a load is present in a tunnel, and the like.

Note that, when the concentration $Cg_2$ of the second gas is equal to or less than the threshold value $Cg_{2\_th}$ in Step S17, the processing proceeds to Step S13, and it is determined that there is no abnormality.

(Effect of Second Example Embodiment)

According to the present example embodiment, similarly to the first example embodiment, in addition to an increase in a concentration of the first gas generated in an early stage of a fire and a smoke concentration, an effect similar to that in the first example embodiment can be acquired by also adding, as a determination indicator, a concentration of the second gas having a generation amount being increased as the fire progresses, and thereby determining a progress situation of the fire. Further, according to the present example embodiment, by also adding an environmental temperature T as a determination indicator, when an environmental temperature is a low temperature in a case where a concentration of the first gas is low and a concentration of the second gas is high, for example, it can be determined that no fire breaks out, and a false alarm can be avoided. Further, a false alarm can be avoided by processing of calculating a spectral width without installing a temperature sensor at various places.

Third Example Embodiment

Next, a third example embodiment according to the present invention will be described by using FIGS. 6 and 7. In the third example embodiment, measurement of two kinds of gas concentrations is performed by switching an output wavelength by time division by using one laser light source.

(Configuration of Third Example Embodiment)

Figure 6:
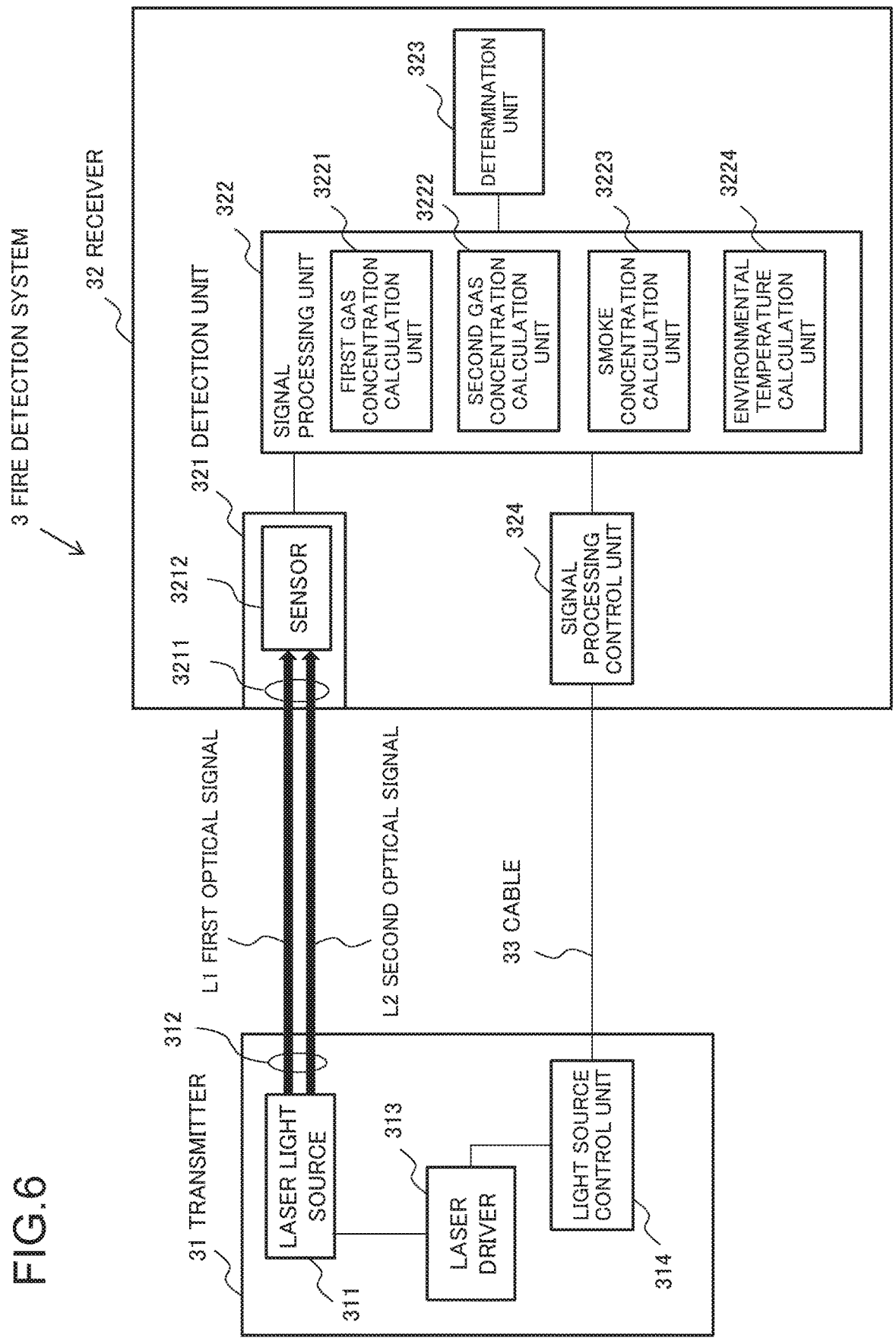
FIG. 6 is a block diagram illustrating a configuration of a third example embodiment according to the present invention.

FIG. 6 is a block diagram illustrating a configuration of the present example embodiment. In a fire detection system 3 in the present example embodiment, as illustrated in FIG. 6, a transmitter 31 is formed of one laser light source 311, one condenser 312, one laser driver 313, and a light source control unit 314. A receiver 32 includes a detection unit 321, one signal processing unit 322, a determination unit 323, and a signal processing control unit 324. The light source control unit 314 and the signal processing control unit 324 are coupled each other with a cable 33.

(Operation in Third Example Embodiment)

Figure 7:
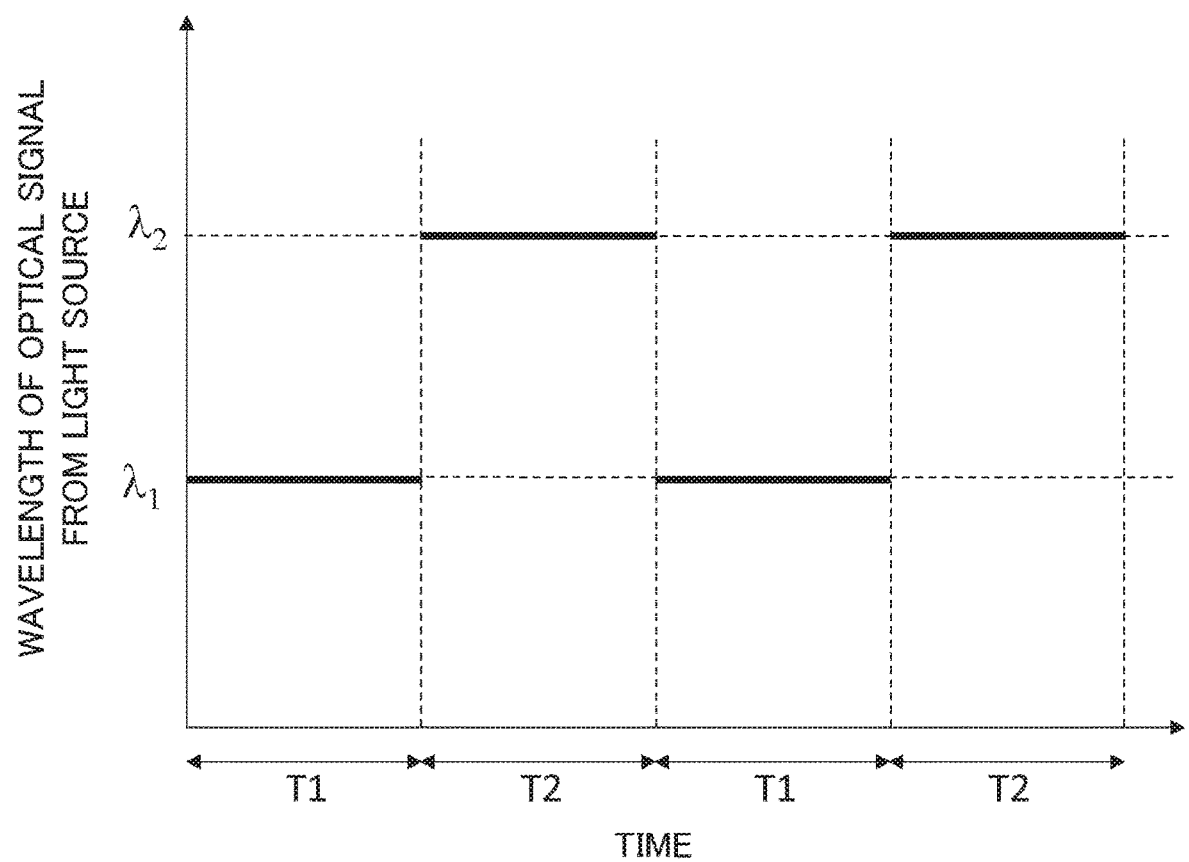
FIG. 7 is a graph illustrating an operation of changing a wavelength of a light source by time in FIG. 6.

FIG. 7 illustrates a time change of an operation wavelength of the laser light source 311. The time information is synchronized between the light source control unit 314 and the signal processing control unit 324.

As illustrated in FIG. 7, the laser light source 311 outputs an optical signal with a wavelength $\lambda_1$ by the laser driver 313 controlling a drive current and a temperature of the laser light source 311 in a period T1. The condenser 312 converts the optical signal with the wavelength $\lambda_1$ into a quasi-parallel light beam. The receiver 32 receives the optical signal propagating through the atmosphere. In the receiver 32, a condenser 3211 of the detection unit 321 condenses the optical signal propagating through the atmosphere, and a sensor 3212 performs photoelectric conversion on the optical signal. A first gas concentration calculation unit of the signal processing unit 322 calculates a concentration $Cg_1$ of a first gas between the transmitter 31 and the receiver 32 from the acquired electric signal. Note that the concentration $Cg_1$ of the first gas may be an average value acquired by measuring the concentration of the first gas for a predetermined period of time. Further, the signal processing unit 322 calculates a smoke concentration Cs between the transmitter 31 and the receiver 32 by using the equation (1) from intensity information about the received optical signal. Furthermore, the signal processing unit 322 calculates an environmental temperature T between the transmitter 31 and the receiver 32 from spread of a width of an absorption spectrum. Note that a measurement of the environmental temperature T in a measuring target space may be performed by a method other than a method of measuring an environmental temperature from spread of an absorption spectrum width, and a different method such as a laser induced fluorometry, for example, may be used.

In a period T2, the laser light source 311 outputs an optical signal with a wavelength $\lambda_2$ by the laser driver 313 controlling a drive current and a temperature, and the condenser 312 converts the optical signal into a quasi-parallel light beam. The receiver 32 receives the optical signal propagating through the atmosphere. In the receiver 32, the condenser 3211 condenses the optical signal, and the sensor 3212 performs photoelectric conversion. The signal processing unit 322 calculates a concentration $Cg_2$ of a second gas between the transmitter 31 and the receiver 32 from the acquired electric signal. Note that the concentration $Cg_2$ of the second gas may be an average value acquired by measuring the concentration of the second gas for a predetermined period of time. Further, the signal processing unit 322 calculates the smoke concentration Cs between the transmitter 31 and the receiver 32 by using the equation (1) from intensity information about the received optical signal. Furthermore, the signal processing unit 322 calculates the environmental temperature T between the transmitter 31 and the receiver 32 from spread of a width of an absorption spectrum. Note that a measurement of the environmental temperature T in a measuring target space may be performed by a method other than a method of measuring an environmental temperature from spread of an absorption spectrum width, and a different method such as a laser induced fluorometry, for example, may be used.

In the determination unit 323, a flow of determining a fire situation from each piece of measurement data is performed similarly to that in FIG. 5.

(Effect of Third Example Embodiment)

According to the present example embodiment, similarly to the first and second example embodiments, in addition to an increase in a concentration of the first gas generated in an early stage of a fire and a smoke concentration, an effect similar to that in the first example embodiment can be acquired by also adding, as a determination indicator, a concentration of the second gas having a generation amount being increased as the fire progresses, and thereby determining a progress situation of the fire. Further, according to the present example embodiment, by also adding an environmental temperature T as a determination indicator, when an environmental temperature is a low temperature in a case where a concentration of the first gas is low and a concentration of the second gas is high, for example, it can be determined that no fire breaks out, and a false alarm can be avoided, similarly to the second example embodiment. Further, a false alarm can be avoided by processing of calculating a spectral width without installing a temperature sensor at various places.

Furthermore, according to the present example embodiment, a concentration of a plurality of gases can be measured by a pair of the laser light source and the optical receiver.

Note that the cable 33 is used in order to synchronize the light source control unit 314 and the signal processing control unit 324 in the description above, however, synchronization communication may be performed in a wireless manner. Further, the light source control unit 314 and the signal processing control unit 324 may each possess a precision clock such as an atomic clock.

Fourth Example Embodiment

Next, a fourth example embodiment according to the present invention will be described by using FIGS. 8 and 9. In the present example embodiment, a third gas concentration calculation unit that measures a concentration of a third gas being a gas consumed by a fire is further provided.

(Configuration of Fourth Example Embodiment)

Figure 8:
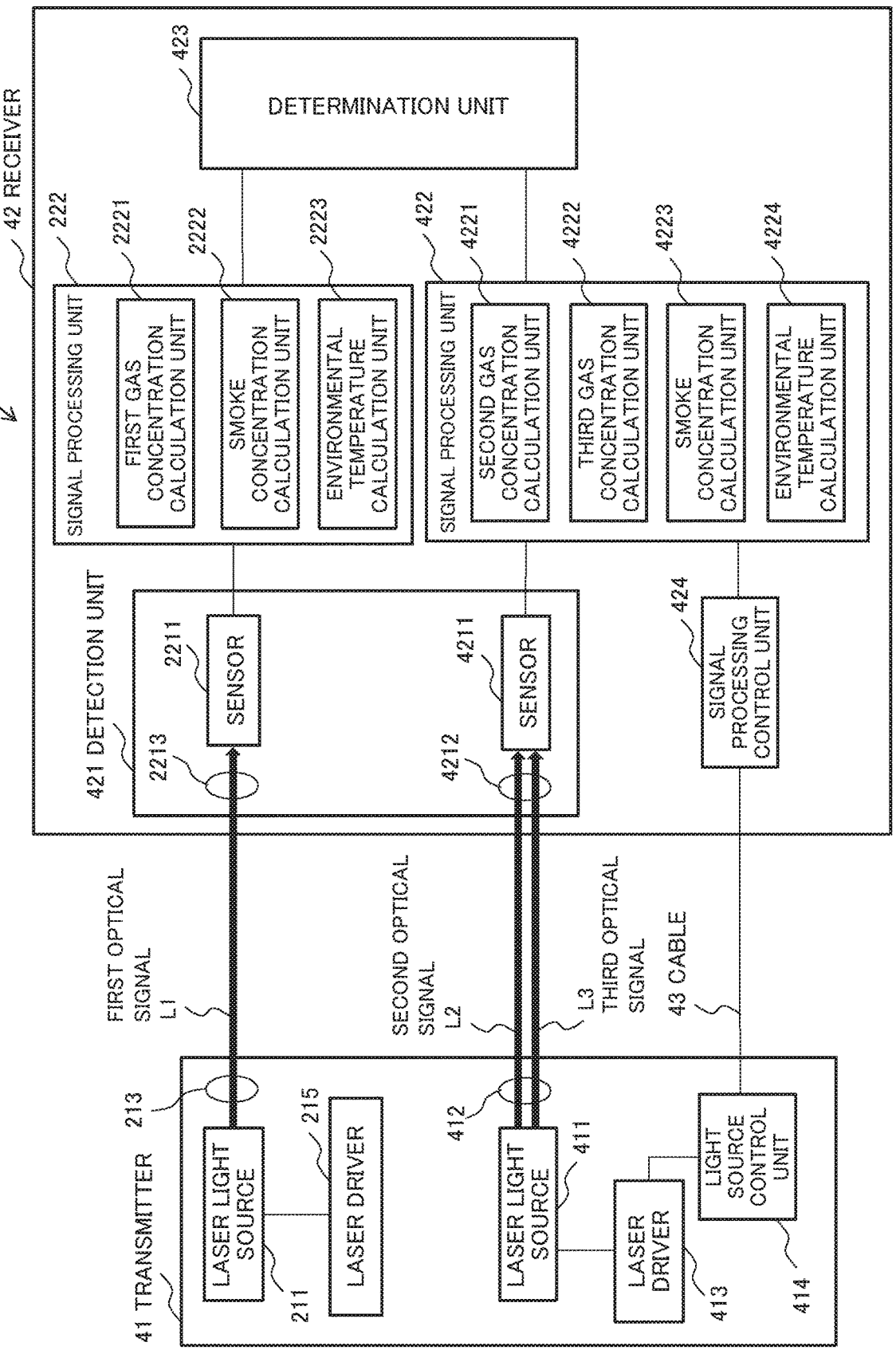
FIG. 8 is a block diagram illustrating a configuration of a fourth example embodiment according to the present invention.

FIG. 8 is a block diagram illustrating a configuration of the present example embodiment. There is described the example embodiment in which a fire detection system 4 in the present example embodiment calculates concentrations of carbon monoxide as a first gas, carbon dioxide as a second gas, and oxygen as a third gas, for example.

As illustrated in FIG. 8, a transmitter 41 in the fire detection system in the present example embodiment includes a laser light source 211 that outputs an optical signal with a wavelength $\lambda_1$ absorbed by the first gas, carbon monoxide, for example, a condenser 213 that converts the optical signal with the wavelength $\lambda_1$ into a quasi-parallel light beam, and a laser driver 215 that controls a drive current and a temperature of the laser light source 211, similarly to the first example embodiment. In addition, the transmitter 41 also includes: a laser light source 411 capable of outputting optical signals L2 and L3 including wavelengths $\lambda_2$ and $\lambda_3$ absorbed by the second gas, carbon dioxide, for example, and the third gas, oxygen, for example; a condenser 412 that converts the optical signals L2 and L3 including the wavelengths $\lambda_2$ and $\lambda_3$ into quasi-parallel light beams; a laser driver 413 that controls a drive current and a temperature of the laser light source 411; and a light source control unit 414.

A receiver 42 includes a detection unit 421, a signal processing unit 222, a signal processing unit 422, a determination unit 423, and a signal processing control unit 424. The light source control unit 414 and the signal processing control unit 424 are coupled each other with a cable 43. An operation wavelength of the laser light source 411 exhibits a time change similar to that in FIG. 7. The time information is synchronized between the light source control unit 414 and the signal processing control unit 424.

For example, the laser light source 411 outputs the optical signal with the wavelength $\lambda_2$ by the laser driver 413 controlling a drive current and a temperature of the laser light source 411 in a period $T_3$. The laser light source 411 outputs the optical signal with the wavelength $\lambda_3$ by the laser driver 413 controlling a drive current and a temperature of the laser light source 411 in a period $T_4$.

The detection unit 421 includes a sensor 2211 and a condenser 2213 similar to those in the second example embodiment, and also includes a sensor 4211 capable of receiving the optical signals L2 and L3 including the wavelengths $\lambda_2$ and $\lambda_3$ absorbed by the second gas, carbon dioxide, for example, and the third gas, oxygen, for example, and a condenser 4212 that condenses the optical signals L2 and L3 including the wavelengths $\lambda_2$ and $\lambda_3$. Further, the signal processing unit 222 is similar to that in the first example embodiment. The signal processing unit 422 includes: a second gas concentration calculation unit 4221 that calculates a concentration $Cg_2$ of the second gas in a measuring target space from an intensity of the optical signal L2 output from the sensor 4211 of the detection unit 421; a third gas concentration calculation unit 4222 that calculates a concentration $Cg_3$ of the third gas in the measuring target space from an intensity of the optical signal L3 output from the sensor 4211 of the detection unit 421; a smoke concentration calculation unit 4223 that calculates a smoke concentration Cs in the measuring target space by using the equation (1) from intensity information about the received optical signal; and an environmental temperature calculation unit 4224 that calculates an environmental temperature T in the measuring target space from an absorption spectrum width of at least one of the three optical signals of the optical signals L2 and L3 output from the sensor 4211 of the detection unit 421. Note that a measurement of the environmental temperature T in the measuring target space may be performed by a method other than a method of measuring an environmental temperature from an absorption spectrum width, and a different method such as a laser induced fluorometry, for example, may be used.

(Operation in Fourth Example Embodiment)

Figure 9:
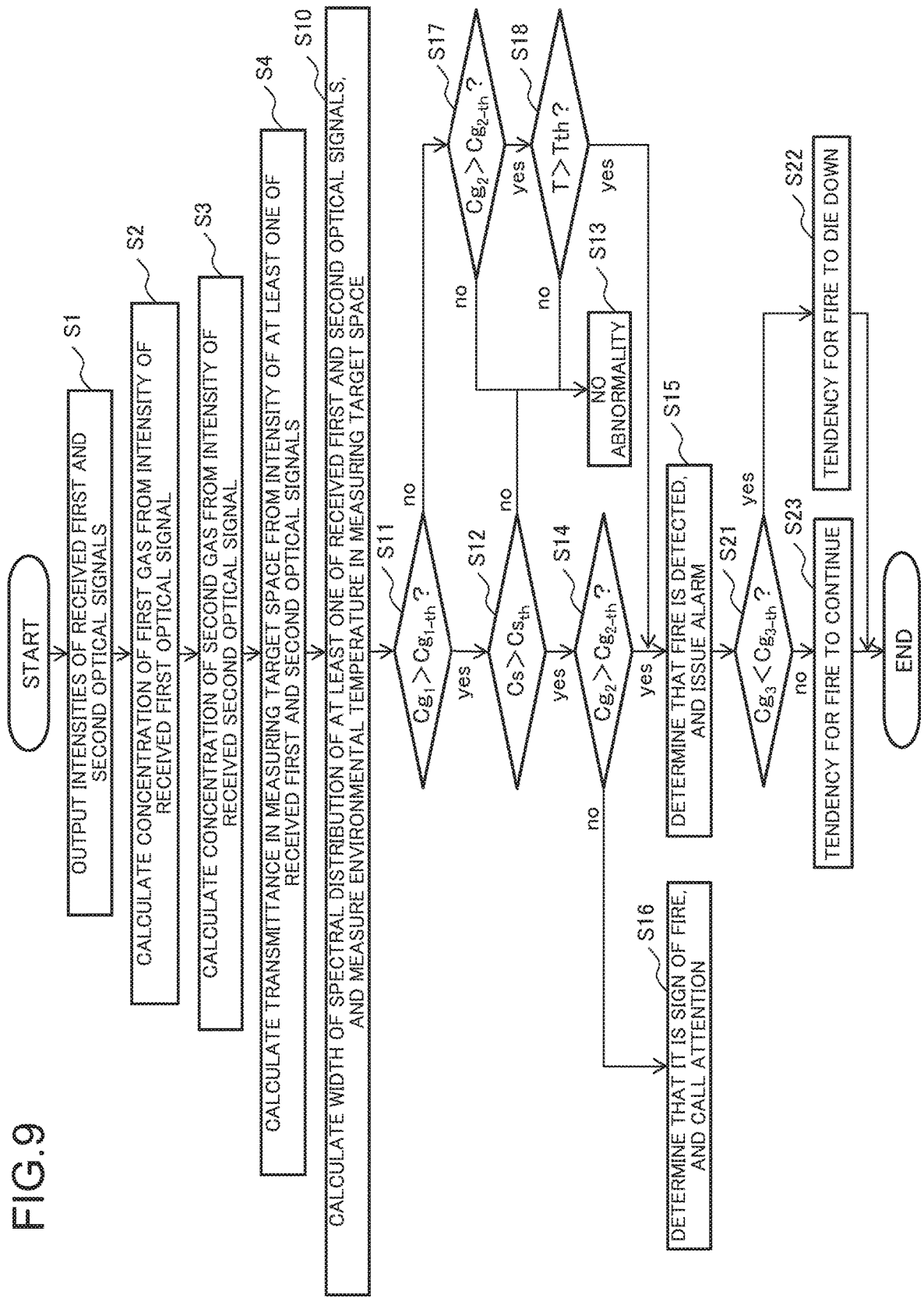
FIG. 9 is a flowchart illustrating an operation of FIG. 8.

FIG. 9 is a flowchart illustrating an operation of FIG. 8. In the present example embodiment, first, processing from Steps S1 to S18 is performed as follows, similarly to the second example embodiment. First, when the laser light sources 211 and 411 of the transmitter 41 emit the first optical signal L1 and the second optical signal L2 or the third optical signal L3 into the measuring target space, respectively, the sensor 2211 of the detection unit 421 of the receiver 42 receives the first optical signal L1 propagating through the measuring target space, and the sensor 4211 of the detection unit 421 receives the second optical signal L2 or the third optical signal L3 propagating through the measuring target space. The sensor 2211 of the detection unit 421 outputs an intensity of the received first optical signal L1 to the signal processing unit 222, and the sensor 4211 of the detection unit 421 outputs an intensity of the received second optical signal L2 or the received third optical signal L3 to the signal processing unit 422 (Step S1).

The first gas concentration calculation unit 2221 of the signal processing unit 222 calculates a concentration $Cg_1$ of the first gas from the intensity of the received first optical signal L1, and outputs the concentration $Cg_1$ to the determination unit 423 (Step S2). Further, the second gas concentration calculation unit 4221 calculates a concentration $Cg_2$ of the second gas from the intensity of the received second optical signal L2 in the period $T_3$ in which the intensity of the second optical signal L2 is output from the sensor 4211, and outputs the concentration $Cg_2$ to the determination unit 423. Further, the second gas concentration calculation unit 4221 calculates a concentration $Cg_3$ of the third gas from the intensity of the received third optical signal L3 in the period $T_4$ in which the intensity of the third optical signal L3 is output from the sensor 4211, and outputs the concentration $Cg_3$ to the determination unit 423 (Step S3). The concentration $Cg_1$ of the first gas, the concentration $Cg_2$ of the second gas, and the concentration $Cg_3$ of the third gas may be average values acquired by respectively measuring the first, second, and third gas concentrations for a predetermined period of time.

Further, the smoke concentration calculation unit 2222 of the signal processing unit 222 calculates a smoke concentration in the measuring target space from the intensity of the received first optical signal L1, and outputs the smoke concentration to the determination unit 224. Further, the smoke concentration calculation unit 4223 of the signal processing unit 422 calculates a smoke concentration in the measuring target space from the intensity of the received second optical signal L2 in the period $T_3$ in which the intensity of the second optical signal L2 is output from the sensor 4211, and outputs the smoke concentration to the determination unit 224. Further, the smoke concentration calculation unit 4223 of the signal processing unit 422 calculates a smoke concentration in the measuring target space from the intensity of the received third optical signal L3 in the period $T_4$ in which the intensity of the third optical signal L3 is output from the sensor 4211, and outputs the smoke concentration to the determination unit 224 (Step S4).

Then, the environmental temperature calculation unit 2223 calculates a spectral width of the received first optical signal L1 from the intensity (spectrum) of the received first optical signal L1, and performs a measurement of the environmental temperature T in the measuring target space. Further, the environmental temperature calculation unit 4224 calculates a spectral width of the received second optical signal L2 from the intensity (spectrum) of the received second optical signal L2 in the period $T_3$ in which the intensity of the second optical signal L2 is output from the sensor 4211, and performs a measurement of the environmental temperature T in the measuring target space. Further, the environmental temperature calculation unit 4224 calculates a spectral width of the received third optical signal L3 from the intensity (spectrum) of the received third optical signal L3 in the period $T_4$ in which the intensity of the third optical signal L3 is output from the sensor 4211, and performs a measurement of the environmental temperature T in the measuring target space (Step S10). Note that a measurement of the environmental temperature T in the measuring target space may be performed by a method other than a method of measuring an environmental temperature from an absorption spectrum width, and a different method such as a laser induced fluorometry, for example, may be used.

Next, the determination unit 423 performs a comparison between the concentration $Cg_1$ of the first gas and a preset threshold value $Cg_{1\_th}$ to (Step S11). When the concentration $Cg_1$ of the first gas exceeds the threshold value $Cg_{1\_th}$, the determination unit 423 calculates a smoke concentration Cs from at least one of a smoke concentration $Cs_1$ from the smoke concentration calculation unit 2222 of the signal processing unit 222 and smoke concentrations $Cs_2$ and $Cs_3$ from the smoke concentration calculation unit 4223 of the signal processing unit 422, and performs a comparison between the smoke concentration Cs and a preset threshold value $Cs_{th}$ (Step S12). When the smoke concentration Cs is equal to or less than the threshold value $Cs_{th}$, the determination unit 423 determines that there is no abnormality (Step S13). For example, when the first gas is carbon monoxide, this corresponds to a case in which a concentration of the first gas in a tunnel rises due to exhaust gas of an automobile, and the like.

When the smoke concentration Cs exceeds the threshold value $Cs_{th}$ in Step S12, the determination unit 224 further performs a comparison between the concentration $Cg_2$ of the second gas and a preset threshold value $Cg_{2\_th}$ (Step S14). When the concentration $Cg_2$ of the second gas exceeds the threshold value $Cg_{2\_th}$, the determination unit 224 determines that a fire is detected, and issues an alarm to a monitor (Step S15).

When the concentration $Cg_2$ of the second gas is equal to or less than the threshold value $Cg_{2\_th}$ in Step S14, the determination unit 423 determines that a sign of a fire is detected, and calls the monitor's attention (Step S16). For example, when the first gas is carbon monoxide, this corresponds to a case in which carbon monoxide is mainly generated before a fire breaks out, and the like.

Next, when the concentration $Cg_1$ of the first gas is equal to or less than the threshold value $Cg_{1\_th}$ in Step S11, the determination unit 424 performs a comparison between the concentration $Cg_2$ of the second gas and the preset threshold value $Cg_{2\_th}$ (Step S17). When the concentration $Cg_2$ of the second gas exceeds the threshold value $Cg_{2\_th}$, the determination unit 423 performs a comparison between the measured environmental temperature T and a preset threshold value $T_{th}$ (Step S18).

When the environmental temperature T exceeds the threshold value $T_{th}$, the processing proceeds to Step S15, and it is determined that a fire is detected, and an alarm is issued. When the environmental temperature T is equal to or less than the threshold value $T_{th}$, the processing proceeds to Step S13, and it is determined that there is no abnormality. For example, when the second gas is carbon dioxide, this is related to a case in which exhaust gas of an automobile or a vehicle loaded with dry ice as a load is present in a tunnel, and the like.

Note that, when the concentration $Cg_2$ of the second gas is equal to or less than the threshold value $Cg_{2\_th}$ in Step S17, the processing proceeds to Step S13, and it is determined that there is no abnormality.

In the present example embodiment, as illustrated in FIG. 9, after a fire alarm is issued in Step S15, a concentration $Cg_3$ of the third gas, oxygen, for example, is compared with a preset threshold value $Cg_{3\_th}$, and whether the concentration $Cg_3$ of the third gas is lower than the preset threshold value $Cg_{3\_th}$ is determined (Step S21). When the concentration $Cg_3$ of the third gas is lower than the threshold value $Cg_{3\_th}$, the monitor is notified that a fire tends to die down (Step S22). When the concentration $Cg_3$ of the third gas is equal to or greater than the threshold value $Cg_{3\_th}$ in Step S21, the monitor is notified that the fire tends to continue (Step S23).

(Effect of Fourth Example Embodiment)

According to the present example embodiment, similarly to the first, second, and third example embodiments, in addition to an increase in a concentration of the first gas generated in an early stage of a fire and a smoke concentration, an effect similar to that in the first example embodiment can be acquired by also adding, as a determination indicator, a concentration of the second gas having a generation amount being increased as the fire progresses, and thereby determining a progress situation of the fire. Further, according to the present example embodiment, by also adding an environmental temperature T as a determination indicator, when an environmental temperature is a low temperature in a case where a concentration of the first gas is low and a concentration of the second gas is high, for example, it can be determined that no fire breaks out, and a false alarm can be avoided, similarly to the second example embodiment. Further, a false alarm can be avoided by processing of calculating a spectral width without installing a temperature sensor at various places.

Furthermore, according to the present example embodiment, calculating concentrations of carbon monoxide as the first gas, carbon dioxide as the second gas, and oxygen as the third gas, for example, makes it possible for the monitor to perceive whether a fire tends to continue or the fire tends to die down after the fire is detected.

While the invention has been particularly shown and described with reference to example embodiments thereof, the invention is not limited to these embodiments. It will be understood by those of ordinary skill in the art that various changes in form and details may be made therein without departing from the spirit and scope of the present invention as defined by the claims.

The present invention is not limited to the above-described example embodiments. For example, the laser light source is used as a light source in the description above, but a wide-band light source such as a light emitting diode (LED) and a super luminescent diode (SLD) may be used.

Further, an optical amplifier may be inserted in an output stage of the laser light source and an input stage of a detector. In this way, a signal-to-noise ratio of a received optical signal can be improved, and accuracy of a measurement result can be increased.

Figure 10:
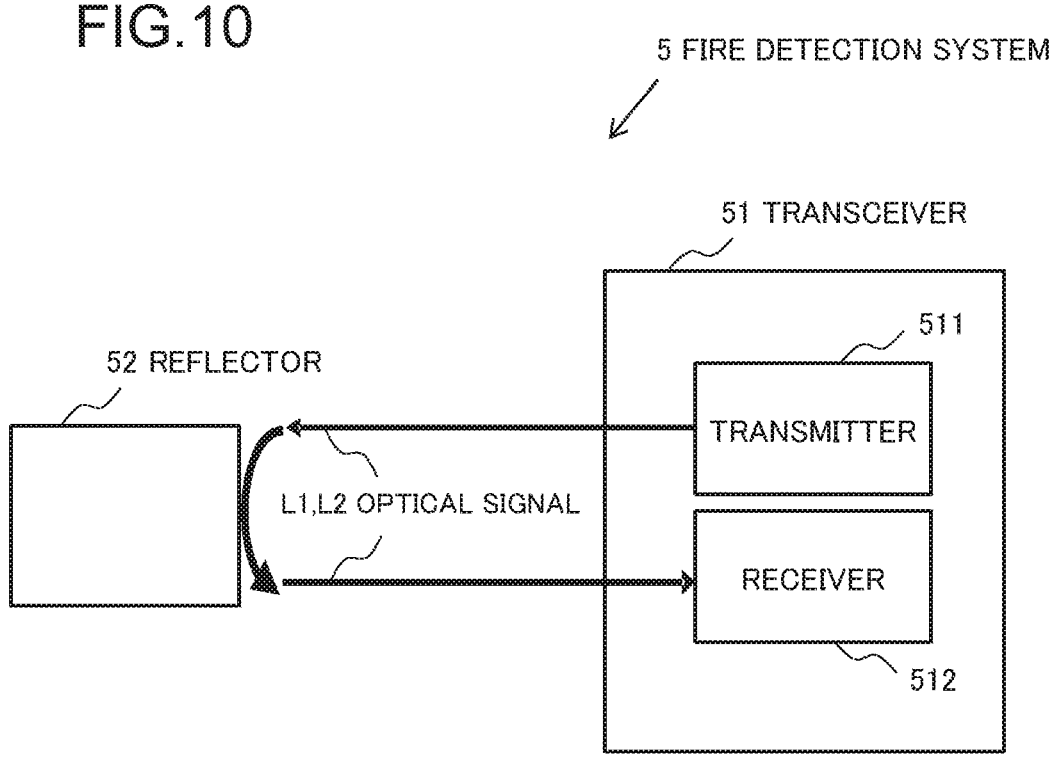
FIG. 10 is a block diagram illustrating a configuration of a reflection-type example embodiment.

Further, a system configuration according to the present invention may be simplified by a reflection-type configuration. FIG. 10 is a block diagram illustrating a configuration of a reflection-type example embodiment. As illustrated in FIG. 10, a reflection-type fire detection system 5 is constituted of a transceiver 51 that houses a transmitter 511 and a receiver 512 of each of the example embodiments described above in one housing, and a reflector 52 that reflects an optical signal from the transmitter 511 to the receiver 512 and causes the optical signal to perform a round-trip propagation between the transceiver 511 and the reflector 52.

This configuration can reduce an influence of an optical axis deviation, and can also set one end to non-power supply. Further, in this way, a target gas having a lower concentration can be detected.

Furthermore, an example of using a concentration of a first gas (carbon monoxide, for example) as a determination indicator of a fire state is described in the description above, but a ratio of a concentration of the first gas to a concentration of a second gas (carbon dioxide, for example) may be used as a determination indicator. In this way, an influence of another environmental fluctuation such as exhaust gas can be reduced.

INDUSTRIAL APPLICABILITY

The present invention is applicable to fire detection in a wide space. Particularly, the present invention is applicable to fire detection in a scene where various ignition sources such as a road tunnel are present and various gases such as exhaust gas are present.

REFERENCE SIGNS LIST 1, 2, 3, 4, 5 Fire detection system
11, 21, 31, 41, 511 Transmitter 12, 22, 32, 42, 512 Receiver
211, 212, 311, 411 Laser light source
213, 214, 2213, 2214, 312, 3211, 412, 4212 Condenser
215, 216, 313, 413 Laser driver
2211, 2212, 3212, 4211 Sensor
222, 223, 322, 422 Signal processing unit
125, 224, 323, 423 Determination unit
314, 414 Light source control unit
324, 424 Signal processing control unit
33, 43 Cable
51 Transceiver
52 Reflector

What is claimed is:

1. A fire detection system, comprising:
a transmitter configured to output a first optical signal including a wavelength absorbed by a first gas generated in an early stage of a fire and a second optical signal including a wavelength absorbed by a second gas having an amount of generation being increased as the fire progresses; and
a receiver including a detector configured to receive the first optical signal and the second optical signal propagating through a measuring target space, a first gas concentration calculator configured to calculate a concentration of the first gas from an intensity of the first optical signal, a second gas concentration calculator configured to calculate a concentration of the second gas from an intensity of the second optical signal, a smoke concentration calculator configured to calculate a smoke concentration from an intensity of at least one of the first optical signal and the second optical signal, and a determination unit configured to determine progress of the fire, based on the concentration of the first gas, the concentration of the second gas, the smoke concentration, and an environmental temperature, wherein
the determination unit further includes an environmental temperature calculator configured to calculate the environmental temperature from an absorption spectral width in a spectrum of the first optical signal and the second optical signal.

2. The fire detection system according to claim 1, wherein the transmitter includes
a light source that outputs the first optical signal and the second optical signal, and
a light source controller configured to control the light source in such a way as to output the first optical signal in a first time period, and output the second optical signal in a second time period, and
the receiver includes a signal processing controller configured to control the first gas concentration calculator in such a way as to calculate a concentration of the first gas from an intensity of the first optical signal received in the first time period, and control the second gas concentration calculator in such a way as to calculate a concentration of the second gas from an intensity of the second optical signal received in the second time period.

3. The fire detection system according to claim 1, wherein the transmitter outputs a third optical signal including a wavelength absorbed by a third gas being a gas consumed by a fire, and
the receiver includes a third gas concentration calculator configured to calculate a concentration of the third gas from an intensity of the third optical signal.

4. The fire detection system according to claim 1, further comprising:
a transceiver configured to house the transmitter and the receiver; and
a reflector configured to reflect an optical signal from the transmitter to the receiver, and causes the optical signal to perform a round-trip propagation between one housing and the reflector.

5. The fire detection system according to claim 1, wherein
the first gas is carbon monoxide,
the second gas is carbon dioxide, and
the determination unit
determines that a sign of a fire appears when a concentration of the first gas and the smoke concentration are greater than a preset threshold value and a concentration of the second gas is equal to or less than a preset threshold value, and
determines that a fire is present when a concentration of the first gas, the smoke concentration, and a concentration of the second gas are greater than a preset threshold value.

6. The fire detection system according to claim 5, wherein,
in a case where a concentration of the first gas is equal to or less than a preset threshold value and a concentration of the second gas is higher than a preset threshold value, the determination unit
determines that a fire is present when the environmental temperature is higher than a preset threshold value, and
determines that there is no abnormality when the environmental temperature is equal to or less than a preset threshold value.

7. The fire detection system according to claim 5, wherein the third gas is oxygen, and,
in a case where a fire is determined to be present, the determination unit determines that a fire tends to die down when a concentration of the third gas is lower than a preset threshold value, and determines that a fire tends to continue when a concentration of the third gas is equal to or greater than a preset threshold value.

8. The fire detection system according to claim 2, wherein
the transmitter outputs a third optical signal including a wavelength absorbed by a third gas being a gas consumed by a fire, and
the receiver includes a third gas concentration calculator configured to calculate a concentration of the third gas from an intensity of the third optical signal.

9. The fire detection system according to claim 2, further comprising:
a transceiver configured to house the transmitter and the receiver; and
a reflector configured to reflect an optical signal from the transmitter to the receiver, and causes the optical signal to perform a round-trip propagation between one housing and the reflector.

10. The fire detection system according to claim 2, wherein
the first gas is carbon monoxide,
the second gas is carbon dioxide, and
the determination unit
determines that a sign of a fire appears when a concentration of the first gas and the smoke concentration are greater than a preset threshold value and a concentration of the second gas is equal to or less than a preset threshold value, and
determines that a fire is present when a concentration of the first gas, the smoke concentration, and a concentration of the second gas are greater than a preset threshold value.

11. The fire detection system according to claim 3, further comprising:
a transceiver configured to house the transmitter and the receiver; and
a reflector configured to reflect an optical signal from the transmitter to the receiver, and causes the optical signal to perform a round-trip propagation between one housing and the reflector.

12. The fire detection system according to claim 3, wherein
the first gas is carbon monoxide,
the second gas is carbon dioxide, and
the determination unit
determines that a sign of a fire appears when a concentration of the first gas and the smoke concentration are greater than a preset threshold value and a concentration of the second gas is equal to or less than a preset threshold value, and
determines that a fire is present when a concentration of the first gas, the smoke concentration, and a concentration of the second gas are greater than a preset threshold value.

13. The fire detection system according to claim 4, wherein
the first gas is carbon monoxide,
the second gas is carbon dioxide, and
the determination unit
determines that a sign of a fire appears when a concentration of the first gas and the smoke concentration are greater than a preset threshold value and a concentration of the second gas is equal to or less than a preset threshold value, and
determines that a fire is present when a concentration of the first gas, the smoke concentration, and a concentration of the second gas are greater than a preset threshold value.

14. A fire detection system, comprising:
a transmitter configured to output a first optical signal including a wavelength absorbed by a first gas generated in an early stage of a fire and a second optical signal including a wavelength absorbed by a second gas having an amount of generation being increased as the fire progresses; and
a receiver including a detector configured to receive the first optical signal and the second optical signal propagating through a measuring target space, a first gas concentration calculator configured to calculate a concentration of the first gas from an intensity of the first optical signal, a second gas concentration calculator configured to calculate a concentration of the second gas from an intensity of the second optical signal, a smoke concentration calculator configured to calculate a smoke concentration from an intensity of at least one of the first optical signal and the second optical signal, and a determination unit configured to determine progress of the fire, based on the concentration of the first gas, the concentration of the second gas, the smoke concentration, and an environmental temperature, wherein
the transmitter includes
a light source that outputs the first optical signal and the second optical signal, and
a light source controller configured to control the light source in such a way as to output the first optical signal in a first time period, and output the second optical signal in a second time period, and
the receiver includes a signal processing controller configured to control the first gas concentration calculator in such a way as to calculate a concentration of the first gas from an intensity of the first optical signal received in the first time period, and control the second gas concentration calculator in such a way as to calculate a concentration of the second gas from an intensity of the second optical signal received in the second time period.

15. The fire detection system of claim 14, wherein
the transmitter outputs a third optical signal including a wavelength absorbed by a third gas being a gas consumed by a fire, and
the receiver includes a third gas concentration calculator configured to calculate a concentration of the third gas from an intensity of the third optical signal.

16. The fire detection system of claim 14, further comprising:
a transceiver configured to house the transmitter and the receiver; and
a reflector configured to reflect an optical signal from the transmitter to the receiver, and causes the optical signal to perform a round-trip propagation between one housing and the reflector.

17. The fire detection system of claim 14, wherein
the first gas is carbon monoxide,
the second gas is carbon dioxide, and
the determination unit
determines that a sign of a fire appears when a concentration of the first gas and the smoke concentration are greater than a preset threshold value and a concentration of the second gas is equal to or less than a preset threshold value, and
determines that a fire is present when a concentration of the first gas, the smoke concentration, and a concentration of the second gas are greater than a preset threshold value.

18. The fire detection system of claim 15, further comprising:
a transceiver configured to house the transmitter and the receiver; and
a reflector configured to reflect an optical signal from the transmitter to the receiver, and causes the optical signal to perform a round-trip propagation between one housing and the reflector.

19. The fire detection system of claim 16, wherein
the first gas is carbon monoxide,
the second gas is carbon dioxide, and
the determination unit
determines that a sign of a fire appears when a concentration of the first gas and the smoke concentration are greater than a preset threshold value and a concentration of the second gas is equal to or less than a preset threshold value, and
determines that a fire is present when a concentration of the first gas, the smoke concentration, and a concentration of the second gas are greater than a preset threshold value.

20. A fire detection method comprising:
outputting a first optical signal including a wavelength absorbed by a first gas generated in an early stage of a fire and a second optical signal including a wavelength absorbed by a second gas having an amount of generation being increased as the fire progresses; and
receiving the first optical signal and the second optical signal propagating through a measuring target space;

calculating a concentration of the first gas from an intensity of the first optical signal;
calculating a concentration of the second gas from an intensity of the second optical signal;
calculating a smoke concentration from an intensity of at least one of the first optical signal and the second optical signal;
calculating the environmental temperature from an absorption spectral width in a spectrum of the first optical signal and the second optical signal;
determining progress of the fire, based on the concentration of the first gas, the concentration of the second gas, the smoke concentration, and the environmental temperature.

* * * * *